US006403766B1

(12) United States Patent
Pardee

(10) Patent No.: US 6,403,766 B1
(45) Date of Patent: Jun. 11, 2002

(54) HUMAN ACTIN REGULATORY PROTEINS AND METHODS FOR DETECTION, DIAGNOSIS AND TREATMENT OF DIFFERENT STAGES OF CARCINOGENESIS

(75) Inventor: Joel D. Pardee, Patterson, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/419,485

(22) Filed: Oct. 15, 1999
Prior Publication Data

(22) Filed:

(51) Int. Cl.[7] .......................... C07K 1/00; C07K 14/00; C07K 17/00; A61K 35/14; A61K 38/16
(52) U.S. Cl. ........................................ 530/350; 530/380
(58) Field of Search .................................. 530/350, 380

(56) References Cited

U.S. PATENT DOCUMENTS

| | | | |
|---|---|---|---|
| 5,071,773 A | 12/1991 | Evans et al. |
| 5,104,975 A | 4/1992 | McCormick et al. |
| 5,401,629 A | 3/1995 | Harpold et al. |
| 5,508,265 A | 4/1996 | Stossel et al. |
| 5,532,220 A | 7/1996 | Lee et al. |
| 5,569,588 A | 10/1996 | Ashby et al. |
| RE35,491 E | 4/1997 | Cline et al. |
| 5,851,786 A | 12/1998 | Johnson |

OTHER PUBLICATIONS

Marcu et al. Recombinant Scinderin, an F-Actin Severing protein, increases calcium-induced release of serotonin from permeabilized platelets, an effect blocked by two scinderin-derived actin-binding peptides and phosphatidylinositol4,5-bisphosphate. Blood 87(1):20-24, 1996.*

Hiroaki Onda et al, "Ts2$^{+/-}$ mide develop tumors in multiple sites that express gelsolin and are influenced by genetic background", *the Journal of Clinical Investigation*, vol. 104, No. 6 (1999).

Igor Weber et al, "Cytoskeletal protein mutations and cell motility in Dicotyostelium", *Biochem. Soc. Symp* 65, 245-265 (1999).

Michelle A. Markus et al, "Refined structure of villin 14T and a detailed comparision with other actin-severing domains", *Protein Science* (1997).

Ludwig Eichinger and Michael Schleicher, Characterization of Actin- and Lipid-Binding Domains in Severin, a Ca$^{2+}$-Dependent F-Action Fragmenting Protein, *Biochemistry* (1992) 31, 4779-4787.

Arndt Schnuchel et al, "Structure of Severin Domain 2 in Solution" *JMB* (1995) 247, 21-27.

Ludwig Eichinger et al, Characterization and Cloning of a Dictyostelium Ste20-like Protein Kinase That Phosphorylates the Actin-binding Protein Severin *the Journal of Biological Chemistry* vol. 273, No. 21 (May 1998), 12952-12959.

Paula Ann Folger, "Identification, Isolation and Expression of M-severin, a Novel Actin Filament Severing Protein in Murine Carcinoma Tumors", *Cornell University*, 1996.

* cited by examiner

*Primary Examiner*—Sheela Huff
*Assistant Examiner*—Alana M. Harris
(74) *Attorney, Agent, or Firm*—Hoffmann & Baron, LLP; Irving N. Feit

(57) ABSTRACT

Protein compositions and methods of use are provided for human Severin. The uses include the preparation of polyclonal and monoclonal antibodies for diagnosing and staging the progression of metastatic tumors and other disorders of cellular growth regulation. Also provided are methods of screening to identify potential drug candidate molecules which modulate the human Severin activity and methods of use of such compounds to accelerate wound healing, or to treat a metastasis or growth disorder.

11 Claims, 4 Drawing Sheets

(3 of 4 Drawing Sheet(s) Filed in Color)

Ala Arg Ala Ala Arg Arg Asp Val Thr His Thr Arg Arg Ser Gly Arg Arg Gly Gln Asp
1            5                    10                    15                        20

Val Ser Ala Ile Pro Thr Gly Arg Thr Asp Gly Arg Thr Pro Gln Gly Arg Lys Pro Ala
            25                   30                    35                        40

Pro Thr Ala Pro Leu His Pro Pro Gln His Thr Gly His Thr Arg Ala Leu Arg Pro His
            45                   50                    55                        60

Arg His Thr Arg His Thr Arg Gln Ala Gly Gln Ala His Ala Ser Ala Gly Pro Ala Ala
            65                   70                    75                        80

Pro Ala Thr Gln Thr Arg Thr Ser Arg Arg Gly Gln Asp Val His Pro Pro Arg Ser Arg
            85                   90                    95                        100

Cys Met Cys His Arg Pro Ser Pro Arg Trp Thr Asp Gly Arg Thr His Ala Ile Arg Asp
            105                  110                   115                       120

Pro Asp Pro Thr Pro Ala Ser Thr Gly His Cys Pro His Pro Gln
            125                  130

Figure 1

HUMAN ACTIN REGULATORY PROTEINS AND METHODS FOR DETECTION, DIAGNOSIS AND TREATMENT OF DIFFERENT STAGES OF CARCINOGENESIS

This work was supported by one or more of the following grants: GM32458 from the N.I.H. and Biomedical Support Grant 507-RR 05396. The government has certain rights to this invention.

FIELD OF THE INVENTION

This invention relates to the field of control of cytoskeletal structure and changes in the cytoskeletal structure, especially as it relates to the regulation of cell motility, transformation and tumorigenesis. Specifically the invention relates to human actin-binding regulatory proteins, nucleic acids encoding these proteins, epitopes of these proteins and antibodies specific for these epitopes. The invention also relates to screening methods for the identification of potential drug candidate molecules and the use of such molecules in cancer therapy and the treatment of other disorders of cell motility, cell proliferation, wound healing, growth and division.

BACKGROUND

The conversion of epithelial cells from sessile, non-dividing cells in monolayers to motile, proliferating cells of invasive carcinomas must be tightly coupled to highly regulated rearrangements of the actin cytoskeleton. In malignant carcinoma tumors, invasion of transformed epithelial cells into the underlying connective tissue occurs by cell migration (References 1–3). Metastasis of carcinoma tumors also involves cell migration from the primary tumor site into blood vessels by diapedesis through the vessel endothelium (Ref. 2).

Migration of metastatic tumor cells was clearly described by Waldeyer in 1872 as amoeboid movement (Ref. 4), a form of cell motility that requires coordinated mobilization and remodeling of the actin cytoskeleton by actin-binding proteins (Refs. 5–10). An initial step in cortical actin cytoskeleton rearrangement includes site-specific actin polymerization onto actin filament ends that have been generated by severing or uncapping of existing filaments (Ref. 11). Two families of actin filament fragmenting/capping proteins are presently recognized, the severin/fragmin/gelsolin family containing shared 125 amino acid repeat domains (Refs. 12–16), and the actin depolymerization factor family of ADF (Ref. 17), depactin (Ref. 18), destrin (Ref. 19), and actophorin (Ref. 20). Severin from Dictyostelium amoebae (Refs. 21,22) and fragmin in Physarum slime molds (Ref. 23) are the earliest phylogenetic examples of actin filament fragmenting proteins. The parallel actin severing protein in mammalian cells is gelsolin, an 80 kDa protein derived from duplication of the ancestral severin gene (Ref 24). A cytoplasmic gelsolin is expressed in epithelial cells, fibroblasts and leucocytes, and secreted plasma gelsolin is present in blood (Refs. 5,6,25). In gelsolin, it is the conservation of severin amino acid sequences that accounts for the actin filament severing activity (Refs. 13,26,27).

Gelsolin is implicated in mammalian cell motility by the demonstration that increased expression of gelsolin in fibroblasts by gene transfection proportionally enhances the rate of migration (Ref. 28). Actin binding protein, ABP 120, has also been implicated in cell motility by functional phenotype analysis (Refs. 29,30). Paradoxically, despite the heightened migratory behavior of invasive tumor cells, gelsolin is extensively down-regulated during transformation of mammary epithelium and fibroblasts (Refs. 31,32).

The following patents and scientific publications may be useful in practicing the full scope of the invention. These patents are incorporated herein by reference in their entirety. The scientific literature is cited to give an indication of the available art known to the skilled artisan in the field. These patents and publications are provided for illustrative purposes.

U.S. Pat. No. 5,374,544 is entitled "Mutated skeletal actin promoter." U.S. Pat. No. 5,464,817 is entitled "Methods for reducing the viscosity of pathological mucoid airway contents in the respiratory tract comprising addministering actin-binding compounds with or without DNAse I."

U.S. Pat. No. 5,508,265 entitled "Therapeutic uses of actin-binding compounds" discloses the use of actin-binding compounds, including gelsolin and biologically active fragments thereof in the treatment of actin-related disorders.

U.S. Pat. No. 5,593,964 is entitled "Methods of treating septic shock by preventing actin polymerization."

U.S. Pat. No. 5,656,589 is entitled "Method for the reduction of viscous purulent airway contents in the respiratory tract comprising administering actin-binding compounds with or without DNAse I."

U.S. Pat. No. 5,851,786 is entitled "Product and process to regulate actin polymerization."

U.S. Pat. No. 5,071,773 entitled "Hormone receptor-related bioassays" discloses assay methods using transcriptional reporter genes generally useful for high throughput screening. Such screens may be adapted for use of assays employing genes encoding actin-binding and regulatory proteins in addition to the steroid hormone receptors which act as transcription factors.

U.S. Pat. No. 5,401,629 discloses further screening methods using readouts based on detecting changes in the transcription of reporter genes engineered to express a detectable signal in response to activation by intracellular signaling pathways.

U.S. Pat. No. 5,482,835 entitled "Methods of Testing in Yeast Cells for Agonists and Antagonists of Mammal G protein-Coupled Receptors" discloses methods for screening;

U.S. Pat. No. 5,747,267 also discloses yeast screens and is entitled "Method for Identifying a G Protein-Coupled Glutamate Receptor Agonist and Antagonist";

U.S. Pat. No. 5,750,353 entitled "Assay for Non-peptide Agonists to Peptide Hormone Receptors" discloses further screening methods; as does U.S. Pat. No. 5,925,529 entitled "Method for Discovery of Peptide Agonists";

U.S. Pat. No. 5,744,303 is entitled "Functional Assays for Transcriptional Regulator genes"; and U.S. Pat. No. 5,569, 588 discloses "Methods for Drug Screening".

Andre, E. A., M. Brink, G. Gerisch, G. Isenberg, A. Noegel, M. Schleicher, J. E. Segall, and E. Wallraff. 1989. *J. Cell Biol.* 108: 985–995. Is entitled: "A Dictyostelium mutant deficient in severin, an F-actin fragmenting protein, shows normal motility and chemotaxis".

Yin, H. L. et al. 1990. FEBS LETT. 264(1): 78–80 is entitled "Severin is a gelsolin phenotype".

Jones, J. G., J. Segal and J. Condeelis. 1991. *Experientia-Suppl.* 59: 1–16 is entitled "Molecular analysis of aioeboid chemotaxis: parallel observations in amoeboid phagacytes and metastatic tumor cells."

Eichinger et al. 1991. J. Cell. Biol. 112(4): 665–76 is entitled "Domain structure in actin-binding proteins: expression and functional characterization of truncated severin."

Prendergast, G. C. and E. B. Ziff 1991. EMBO J. 10(4): 757–66 is entitled "Mbh1: a novel gelsolin/severin-related protein which binds actin in vitro and exibits nuclear localization in vivo."

Finidori et al. 1992. J. Cell. Biol. 116(5): 1145–55 is entitled "In vivo analysis of functional domains from villin and gelsolin."

Eichinger, L. and M. Schleicher. 1992. Biochemistry 31(20) 4779–87 is entitled "Characterization of actin- and lipid-binding domains in severin, a Ca(2+)-dependent F-actin fragmenting protein."

Schnuchel et al. 1995. J. Mol. Biol. 247(1): 21–7 is entitled "Structure of severin domain 2 in solution."

Folger, P. A. 1996. Ph.D. thesis, Cornell University, entitled "Identification, isolation and expression of M-severin, a novel actin filament severing preotein in murine carcinoma tumors."

Markus et al. 1997. Protein Sci. 6(6): 1197–1209 is entitled "Refined structure of villin 14T and a detailed comparison with other actin-severing domains."

Eichinger, L. et al. 1998. J. Biol. Chem. 273(21): 12952–9 is entitled "Characterization and cloning of a Dictyostelium Ste20-like protein kinase that phosphorylates the actin-binding protein severin."

Weber, I., Niewohner, J., and Faix, J. 1999. Biochem. Soc. Symp. 65:245–65 is entitled "Cytoskeletal protein mutations and cell motility in Dictyostelium."

Despite a longfelt need to isolate the human actin regulatory proteins corresponding to M-severin and M-30 these these proteins have not been provided until the disclosure of the present invention.

Nowhere in these references is there any disclosure, suggestion or even hint of the use of actin-binding and regulatory proteins including human severin (also herein interchangeably referred to as human M-severin) and human M-30, the activities of which are diagnostic for the particular stage of a proliferative disorder, as screens for modulators of the activity of M-severin, M-30 and other members of the actin-binding regulatory molecules, and the use of such modulators as novel drug candidate molecules.

SUMMARY OF THE INVENTION

The invention provides isolated native or recombinant human actin-binding regulatory proteins which are expressed in motile, proliferating and invasive cells, and in cells at the site of a wound. Cloning and expression of these proteins in recombinant hosts and methods of purification of the recombinant proteins are provided. Methods are also provided for isolation of each of these proteins from human cells, the raising of antibodies thereto and methods of use of these proteins in actin-binding and actin-severing assays.

In a particular embodiment the protein is human M-severin. In a second embodiment the protein is human M-30. The terms human M-severin and human M-30 are used throughout this specification to designate actin-binding regulatory proteins expressed in motile, proliferating and invasive cells, and in cells at a wound site, and fragments of each which retain actin-binding, actin-severing or regulatory function or any combination of these properties. Human M-severin is a protein which cross reacts with antibodies directed against both Dictyostelium and mouse M-severin and has an apparent MW of aprox. 40,000 as assessed by SDS-polyacrylamide gel electrophoresis. Human M-30 protein is an actin-bundling protein which cross reacts with both anti-Dictyostelium M-30 antibodies and anti-mouse M-30 antibodies and exhibits an apparent MW of approximately 34,000 to 35,000 as assessed on SDS-polyacrylamide gels.

Such native or recombinant proteins and active fragments may be at least 90% homologous to the human M-severin or human M-30. Most preferred for practicing the invention are the native or recombinant proteins and active fragments that are preferably at least 95% to 97% homologous to the human M-severin or human M-30. The optimum native or recombinant proteins and active fragments of the latter class are 97% –, 98% or 99% –100% homologous to the human M-severin or human M-30 proteins.

In yet another embodiment the invention provides a native or recombinant human actin-binding regulatory protein expressed in motile, proliferating and invasive cells, and in cells at a wound site or at the site of a healing wound, which is capable of severing F-actin filaments.

In a further embodiment the invention provides a nucleic acid molecule, including both DNA and RNA molecules, encoding a native or recombinant human actin-binding regulatory protein expressed in motile, proliferating and invasive cells, and in cells at the site of a wound or a healing wound. The nucleic acid may comprise a vector in addition to the sequence encoding the native or recombinant human actin-binding regulatory protein. Such nucleic acids of the present invention encompass natural variants, allelles and polymorphs of the human M-severin and human M-30 genes as well as recombinant molecules encoding these variants, allelles and polymorphic forms.

A polyclonal or monoclonal antibody which specifically binds an epitope of a native or recombinant human actin-binding regulatory protein is also provided. Among these monoclonal and polyclonal antibodies are those which specifically bind human M-severin and human M-30. Single chain antibodies which specifically bind an epitope of human M-severin are also provided.

The invention further provides a method of determining the proliferative status or stage of carcinogenesis of a cell, comprising: providing a cell sample from a cell culture, primary cell isolate or biopsy, assessing the levels of M-severin or M-30, and thereby determining the proliferative status of the cell. The level of M-severin or M-30 may be assessed by a northern blot or western blot techniques, or by cytoimmunohistochemistry.

In yet a further embodiment the invention provides a method of identifying a compound as a modulator of M-severin expression or activity, comprising: providing a cell expressing M-severin protein, contacting the cell with a test compound, assessing the activity of the M-severin in the cell, assessing the activity of the M-severin in an identical cell which has not been contacted with the test compound, comparing the two M-severin activities, and thereby determining whether the test compound is a modulator of M-severin activity.

In still yet a further embodiment the invention provides a method of identifying a compound as a modulator of M-30 expression or activity, comprising: providing a cell expressing M-30 protein, contacting the cell with a test compound, assessing the activity of the M-30 in the cell, assessing the activity of the M-30 in an identical cell which has not been contacted with the test compound, comparing the two M-30 activities, and thereby determining whether the test compound is a modulator of M-30 activity.

In yet another embodiment the invention provides a method of treating a mammalian cell in a stage of carcinogenesis comprising: administering an effective amount of a compound which modulates M-severin expression or activity such that carcinogenesis is modulated. Among these compounds are molecules that modulate the actin-binding or actin-severing activity of the human M-severin. Other compounds of this embodiment may function by modulating the transcription of the M-severin.

Further in yet another embodiment the invention provides a method of treating a mammalian cell in a stage of carcinogenensis comprising: administering an effective amount of a compound which modulates M-30 expression or activity such that carcinogenesis is modulated. Among these compounds are molecules that modulate the actin-binding or actin-severing activity of the human M-30. Other compounds of this embodiment may function by modulating the transcription of the M-30.

It should be understood that throughout the specification the terms M-severin and M-30 refer to mammalian severin and M-30, of which human severin and human M-30 are species. Further, the terms M-severin and M-30 refer to both native and recombinant forms of the proteins whether isolated from human cells or from recombinant hosts, which may be eukaryotic or prokaryotic hosts carrying the recombinant nucleic acid sequence encoding M-severin or M-30.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 1. Predicted amino acid sequence of cDNA clone 10c-1. The predicted amino acid sequence of the protein encoded by clone 10 c-1 was determined from the open reading frame (ORF) of the partial cDNA which encodes 135 amino acids (SEQ ID NO.:1).

FIG. 3A: M-severin cytoimmunofluoresence in a dividing and motile LL/2 cell. FIG. 3B: F-actin rhodamine phalloidin staining in a dividing LL/2 cell. M-severin and F-actin colocalized to the leading cell edge and cleavage furrow. FIG. 3C: The dividing cell pair shown in FIG. 3A in vertical section through the cell midline confirms the highest concentrations of M-severin at the leading cell edge and cleavage furrow.

FIGS. 4A, 4B.) Colon serial sections through well-differentiated adenocarcinoma in colonic villi (CV) and underlying connective tissue (CT) containing moderately differentiated adenocarcinoma tumor (AT). FIG. 4A.) Control staining with secondary HRP-conjugated antibody and hematoxylin shows cell nuclei (blue) only. FIG. 4B.) M-severin staining with hematoxylin counterstain shows M-severin expression in the basal aspect of epithelial cells of well-differentiated adenocarcinoma (CV), throughout cells of moderately differentiated adenocarcinoma (AT), and in fibroblasts of the connective tissue (CT). FIG. 4C, FIG. 4D.) Low (FIG. 4C, 100×) and high (FIG. 4D, 600×) magnification of normal colon epithelium at the surgical margin of a resected tumor. Normal epithelial cells carry hematoxylin stained nuclei, but do not express M-severin (FIG. 4D, arrows). M-severin staining is apparent in fibroblasts (FIG. 4D, *) of the lamina propria subjacent to the basement membrane of colonic epithelial cells. FIGS. 4E, 4F). Low power (FIG. 4E, 100×) and high power (FIG. 4F, 600×) magnification of moderately differentiated adenocarcinoma containing M-severin. FIGS. 4G, 4H.) Low power (FIG. 4G, 10×) and high power (FIG. 4H, 600×) magnification of undifferentiated adenocarcinoma (FIG. 4G, arrow) showing heavy expression of M-severin. Comparison of normal epithelium with moderately differentiated adencarcinoma and undifferentiated carcinoma (FIGS. 4D, 4F. and 4H., respectively) indicates enhanced expression of M-severin in advancing stages of tumor progression.

DETAILED DESCRIPTION

Figure 2:
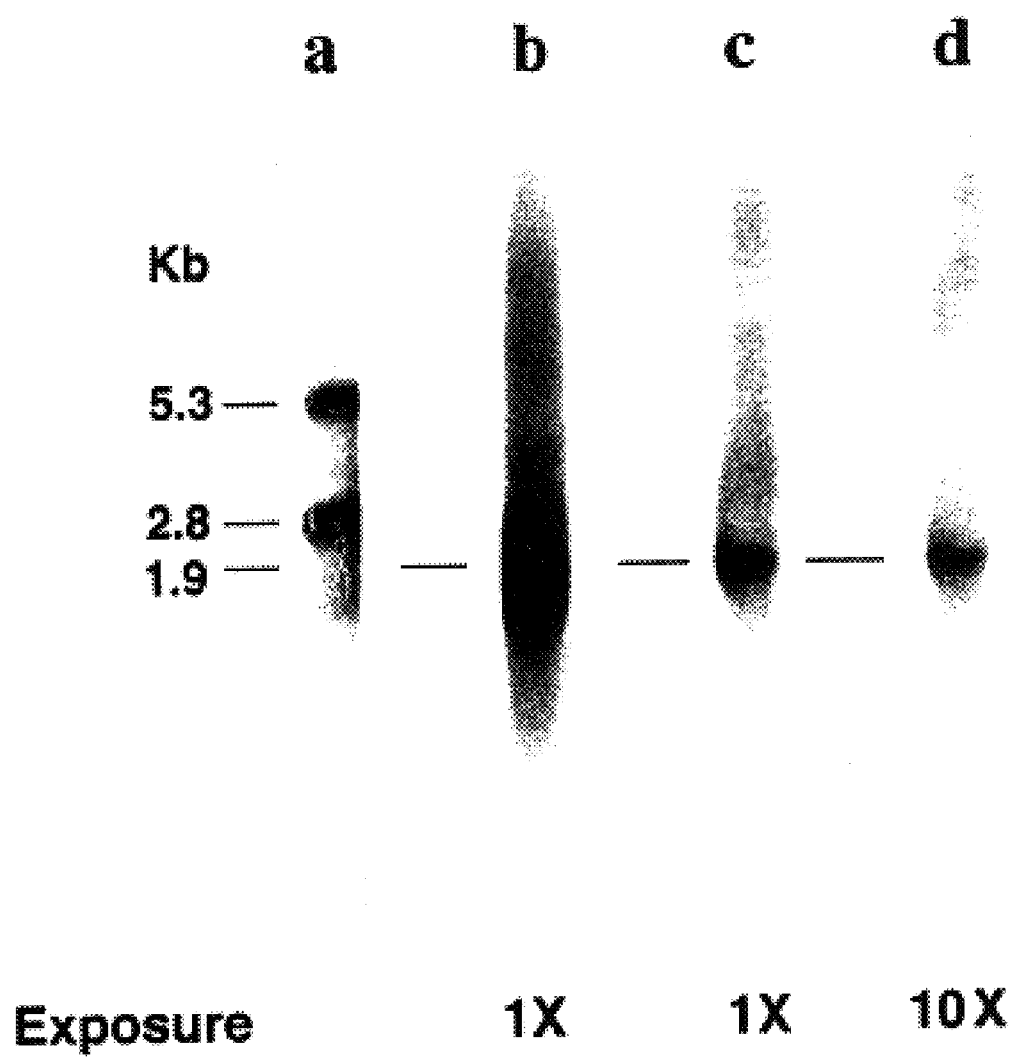
FIG. 2. M-severin mRNA Expression Increases with Metastatic Potential of Epithelial Cells. Comparative expression patterns of M-Severin mRNA in transformed cells of increasing metastatic potential. Equivalent amounts (50 μg) of total RNA prepared from each cell type was probed with a 0.65 kb cDNA of M-severin cloned from a P-19 carcinoembryonic cell library. Blots were exposed for 36 h (1×exposure) followed by a 14 day exposure (10×) in a Molecular Dynamics PhosphorImager. Molecular weight markers are shown (Lane a). A 1.9 kb signal was common to all cell types. Signal strength increased with metastatic potential of the cell line. Highly metastatic P19 cells (Lane b) expressed approximately 7-fold more M-severin mRNA than weakly metastatic LL/2 cells (Lane c) and 70-fold more M-severin than immortalized MDCK cells (Lane d).

According to methods of the present invention actin-binding, actin-severing regulatory proteins may be isolated by methods presented herein in the Examples section of this specification. Human M-severin is prepared in an identical manner to the method of preparation of M-severin from (mouse) Lewis lung adenocarcinoma tumor cells (as described below). The human M-severin is cross reactive with antibodies raised against Dictyostelium severin and also with antibodies raised against mouse M-severin and exhibits actin-binding and actin-severing activities. The human M-severin protein is particularly highly expressed in tumor cells, somewhat less well expressed in adenocarcinoma cells and even less well expressed in well differentiated pre-adenocarcinoma cells.

Specifically, the isolation and uses of human M-severin of MW approx. 40,000 and the human M-30 of approx. MW 35,000 are presented. These proteins may be used in the methods of the present invention to raise antibodies for diagnosis and staging of metastatic disease, for assays and screens for compounds which modulate actin-binding, actin-severing or other actin regulatory functions. Compunds identified by such assays and screens may be used in management and treatment of disorders of cell proliferation, growth and metastasis by inhibiting human M-severin function or human M-30 function. Alternatively, wound healing may be accelerated by enhancing the function of human M-severin function or human M-30.

The inhibition of cell proliferation may occur in the method of the invention by means of any mechanism. For example, the molecules identified by the methods of the present invention may act as neutral antagonists of a mammalian severin or M-30 activity. Another type of antagonist is called a negative antagonist (or inverse agonist). Alternatively, particularly for applications in wound healing, the molecules may act as agonists by stimulating or activating the mammalian severin or M-30 activity.

The molecules identified by the methods of the present invention may be small molecules or biological molecules. Such biological molecules include all lipids and polymers of monosaccharides, amino acids and nucleotides having a molecular weight up to 300 or even 450 daltons. Thus, biological molecules include, for example, fragments of oligosaccharides and polysaccharides; oligopeptides, polypeptides, peptides, and proteins; and oligonucleotides and polynucleotides. Oligonucleotides and polynucleotides include, for example, DNA and RNA.

Biological molecules further include derivatives of any of the molecules described above. For example, derivatives of biological molecules include lipid and glycosylation derivatives of oligopeptides, polypeptides, peptides and proteins. Derivatives of biological molecules further include lipid and glycosylated derivatives of oligosaccharides and polysaccharides, e.g. lipopolysaccharides.

Any molecule that is not a biological molecule is considered in this specification to be a small molecule. Accordingly, small molecules include organic compounds, organometallic compounds, salts of organic and organometallic compounds, saccharides amino acids, and nucleotides. Small molecules further include molecules that would otherwise be considered biological molecules, except their molecular weight is not greater than 450. Thus, small molecules may be lipids, oligosaccharides, oligopeptides, and oligonucleotides, and their derivatives, having a molecular weight of 450 or less.

It is emphasized that small molecules can have any molecular weight. They are merely called small molecules because they typically have molecular weights less than 450.

Expression of severin and other actin binding proteins may also be monitored by transcription assays employing reporter genes coupled to the promoter of the monitored gene. Reporter genes useful for this embodiment of the methods of the present invention include alkaline phosphatase (AP), luciferase (luci), chloramphenicol acetyl transferase (CAT), β-galacto-sidase (lacZ), and β-lactamase (bla). This list is intended only as a guide and should not be construed as limiting in any way. Any gene which has a detectable product may be used as a reporter gene in the methods of the present invention; especially preferred are those such as AP, luci, CAT, lacZ, and bla for which routine assays are readily available.

Inhibition of proliferation may be assessed qualitatively as a detectable change in growth or proliferation, or quantitatively wherein the detectable change is the difference between a measured proliferation parameter (such as incorporation of $^3$H-thymidine from $^3$H-TTP into chromosomal DNA) the test cell contacted with the test compound and in an identical control untreated cell. Inhibition of proliferation may be scored as detectable in the qualitative assay, or as a 10%, or preferably 50% or 80%, or most preferably 100% inhibition of proliferation in the treated cell as assessed by a quantitative assay.

Contacting the cell may be achieved by adding an effective amount of the compound directly to the culture medium if the cell is a primary cell culture or a cell line in culture. If the cell is present in the intact animal the contacting may be achieved by administering an effective amount of the compound in a pharmaceutically acceptable carrier intravenously (i.v.), interperitoneally (i.p.), or in some embodiments the compound may be administered orally (p.o.) with solid food or liquids, syrups etc. or in mixtures comprising approved carriers, (generally accepted as safe for use in foods).

The screening methods contemplated in the invention include for example, cell-free systems in which the components may be obtained from the tissues of an organism, primary cells, cultured cell lines or from recombinant cells. Prokaryotic organisms including for example: *Escherichia coli* and *Salmonella typhimurium* may be used as recombinant hosts for the production of any or all of the following: Actin-binding regulatory proteins, M-severin or M-30 components specified in the invention. Eukaryotic organisms including yeast (e.g. *Saccharomyces cerevisiae*), the filamentous fungus Aspergillus, and insect cells (e.g. sf9 cells of *Spodoptera frugiperda*), or mammalian cell lines as disclosed herein may also be useful for production of the components used in the methods of this invention. These components may be used in cell-free systems derived from these eukaryotic organisms. Alternatively, these methods, particularly the screening methods, may be carried out using cells in culture or directly in the intact organism.

The invention also provides a method of treatment of a human, having a proliferating tumor or other growth regulation disorder which comprises: administering to the animal an effective amount of a compound capable modulating severin activity such that the proliferation of the tumor is inhibited or the growth regulation disorder is ameliorated.

An effective amount of compound is that amount which upon contacting the cell leads to a detectable change in proliferation or tumor growth and most preferably leads to total suppression of proliferation while causing minimal or no unwanted side-effects in the cell or in the whole animal. An effective amount of compound per weight of cells or body weight may be between 1 and 100 ng/kg, but is preferably between 1 and 100 ug/kg, or between 1 and 100 mg/k, but may also be 1 gm/kg or even 10 gm/kg body weight.

The invention provides methods for the modulation of expression or activity of human severin or of human M-30 and of homologs of each. The homologs are recognized as having at least 90% and preferably 95%, even more preferably 97%, yet more preferably 98% and optimally 99% or greater homology to the human severin or human M-30 proteins. The homologous region is present in either amino acid sequences aligned with a maximum number of identical residues. Gaps and bubbles of sequence may be present in the alignment, but unbroken aligned sequences are preferred and may be identified by visual inspection. Also provided in the invention are naturally occuring polymorphs of human severin or human M-30 as well as the alleles and natural genetic variants in the human population.

Alignments of nucleic acid coding sequences and assessment of the percent homologies may also be performed to provide sequences which may be used in the present invention. Publicly available sequences available from the GenBank database of over 2.5 million sequences comprising over 1.8 billion nucleotides (See Benson et al.

Nucleic Acids Research 27 (1) 12–17 for a description) may be used for searches and alignments of sequences using the BLAST homology search program available on the internet at http://www.ncbi.nlm.nih.gov. Protein and peptide sequences are available from the Protein Research Foundation (PRF), the Protein Data bank (PDB) and the SWISS-PROT database at the National Center for Biotechnology Information (NCBI), a division of the National Library of Medicine (NLM) also accessible from the same web-site.

A persisting paradox in cytoskeletal regulation of cell motility is the loss of the actin filament fragmenting protein, gelsolin, in transformed epithelial cells that have gained the ability to migrate. Either actin filament severing does not occur during motility of carcinoma cells, or a novel fragmentation protein is expressed during transformation. Using an antibody specific for severin, the 40 kDa actin filament severing protein from *Dictyostelium discoideum* amoebae, we have identified a mammalian form of severin in murine LL/2 carcinoma cells lacking gelsolin. Mammalian severin (M-severin) isolated from LL/2-derived Lewis lung carcinoma tumors severed F-actin in a calcium-dependent manner, mimicking the function of Dictyostelum severin. M-severin preferentially localized to the cleavage furrow of dividing LL/2 cells and to the actin-rich cortex of migratory LL/2 cells, known sites of active actin cytoskeleton rearrangement. The mammalian severing protein was fully expressed in transformed LL/2 epithelial cells, but went undetected in normal mouse muscle, liver, spleen or kidney.

Normal mouse lung tissue contained minute amounts of M-severin, attributed to motile cells in pulmonary connective tissue. In striking contrast to M-severin, gelsolin was highly expressed in normal lung, but disappeared in transformed LL/2 carcinoma cells. Based on prior observations of a functional role for actin filament fragmentation in cell migration, the simultaneous induction of M-severin and loss of gelsolin during epithelial transformation suggests that replacement of gelsolin by M-severin may function to achieve actin filament rearrangements necessary for active cell migration in invasive or metastatic carcinoma. Induction of M-severin in an invasive tumor was directly observed in human colon adenocarcinoma by cytoimmunohistochemistry with antibodies directed against severin isolated from both Dictyostelium amoebae and Lewis lung carcinoma cells. Since normal colon epithelium from the same patient did not express M-severin, it may serve as a sensitive marker for detection and staging of epithelial tumors.

We analysed lysates of highly motile and transformed epithelial LL/2 cells together with their resultant Lewis lung carcinoma tumors for the presence of severin, the ancestral actin filament fragmentation protein prominent in Dictyostelium amoebae. The results indicate that both LL/2 cells and their derived tumors contain a mammalian form of severin. Moreover, while gelsolin is dominantly expressed in normal lung epithelium, M-severin appears to become expressed during transformation to replace gelsolin in LL/2 cells and tumors. Furthermore, M-severin expression appears to be a general feature of motile and/or transformed epithelial cells, but not of non-motile cells of muscle, liver or normal epithelium. It is this specificity for motile cells that makes M-severin useful for marking invasive carcinoma tumors. Consequently, we further show that invasive human colon adenocarcinoma tumors contain abundant levels of M-severin, and M-30 while normal colon epithelium from the same patient do not express the protein.

EXAMPLES

General Methods

Preparation of Protein

The protein and fragments of the present invention may be prepared by methods known in the art. Such methods include isolating the protein directly from cells, isolating or synthesizing DNA encoding the protein and using the DNA to produce recombinant protein, and synthesizing the protein chemically from individual amino acids.

A. Isolation of Protein from Solution

Proteins are isolated from the solubilized fraction by standard methods. Some suitable methods include precipitation and liquid/chromatographic protocols such as ion exchange, hydrophobic interaction and gel filtration See, for example, Guide to Protein Purification, Deutscher, M. P. (Ed.) Methods Enzymol., 182, Academic Press, Inc., New York (1990) and Scopes, R. K. and Cantor, C. R. (Eds.), Protein Purification (3d), Springer-Verlag, New York (1994).

B. Isolation of Protein from Gels

Alternatively, purified material is obtained by separating the protein on preparative SDS-PAGE gels, slicing out the band of interest and electroeluting the protein from the polyacrylamide matrix by methods known in the art. The detergent SDS may be removed from the protein by known methods, such as by dialysis or the use of a suitable column, such as the Extracti-Gel column from Pierce Chemical Company.

C. Chemical Synthesis of Protein

The proteins of the invention and DNA encoding the proteins may also be chemically synthesized by methods known in the art. Suitable methods for synthesizing the protein are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Suitable methods for synthesizing DNA are described by Caruthers in Science 230:281–285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

RECOMBINANT PROTEIN

The protein may also be prepared by providing DNA that encodes the protein; amplifying or cloning the DNA in a suitable host; expressing the DNA in a suitable host; and harvesting the protein and in certain embodiments, purifying the protein.

A. Providing DNA

1. Chemical Synthesis from Nucleotides

The DNA may be synthesized chemically from the four nucleotides (A, T. G and C) in whole or in part by methods known in the art. Such methods include those described by Caruthers in Science 230:281–285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992).

Alternatively, the nucleic acid molecules of the invention may be isolated from the available cDNA libraries and screened with selected probes designed to identify the gene of interest. See Sambrook, J. et al. (eds), Molecular Cloning, Second Edition, Cold Spring Harbor Laboratory Press, Cold Spring Harbor, N.Y. (1989) and Ausubel, F. M. et al. (eds), Current Protocols in Molecular Biology, John Wiley & Sons, New York (1999).

DNA may also be synthesized by preparing overlapping double-stranded oligonucleotides, filling in any gaps with polymerase I, and ligating the ends together with DNA ligase. The DNA may be cloned in a suitable host cell and expressed in the same cell or isolated and transformed in a host cell more suitable for expression. The DNA and protein may be recovered from the host cell. See, generally, Sambrook, J. et al. (Eds.), Molecular Cloning, Second Edition, Cold Spring Harbor Laboratory Press, Cold Spring Harbor, N.Y. (1989) and Ausubel, F. M. et al. (Eds.), Current Protocols in Molecular Biology, John Wiley & Sons, Inc., New York (1999).

B. Expressing DNA

The DNA encoding the protein of the invention may be replicated and used to express recombinant protein following insertion into a wide variety of host cells in a wide variety of cloning and expression vectors. The host may be prokaryotic or eukaryotic. The DNA may be obtained from natural sources and, optionally, modified. The genes may also be synthesized in whole or in part.

Cloning vectors may comprise segments of chromosomal, non-chromosomal and synthetic DNA sequences. Some suitable prokaryotic cloning vectors include plasmids from *E. coli,* such as colE1, pCR1, pBR322, pMB9, pUC, pKSM, and RP4. Prokaryotic vectors also include derivatives of phage DNA such as lambda and M13 or fd, and other filamentous single-stranded DNA phages.

Vectors for expressing proteins in bacteria, especially *E.coli,* are also known. Such vectors include the pK233 (or any of the tac family of plasmids), T7, pBluescript II, bacteriophage lambda ZAP, and lambda $P_L$ (Wu, R. (Ed.), Recombinant DNA Methodology II, Methods Enzymol., Academic Press, Inc., New York, (1995)). Examples of vectors that express fusion proteins are PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. [see addition from SKE-1-P] Other expression vector systems are based on beta-galactosidase (pEX); maltose binding protein (pMAL); glutathione S-transferase (pGST or PGEX)—see Smith, D. B. Methods Mol. Cell Biol. 4:220–229 (1993); Smith, D. B. and Johnson, K. S., Gene 67:31–40 (1988); and Peptide Res. 3:167 (1990), and TRX (thioredoxin) fusion protein (TRXFUS)—see LaVallie, R. et al., Bio/Technology 11 197–193 (1993).

Vectors useful for cloning and expression in yeast are available. Suitable examples are 2 μm circle plasmid, Ycp50, Yep24, Yrp7, Yip5, and pYAC3 (Ausubel, F. M. et al. (Eds.), Current Protocols in Molecular Biology, John Wiley & Sons, Inc., New York, (1999)).

Suitable cloning/expression vectors for use in mammalian cells are also known. Such vectors include well-known derivatives of SV-40, adenoviris, cytomegalovirus (CMV) retrovinis-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P. Berg, J. Mol. Appl. Genet. 1:327–341 (1982); S. Subramani et al, Mol. Cell. Biol. 1:854–864 (1981); R. J. Kaufmann and P. A. Sharp, "Amplification And Expression Of Sequences Cotransfected with A Modular Dihydrofolate Reductase Complementary DNA Gene," J. Mol. Biol. 159:601–621 (1982); R. J. Kaufynann and P. A. Sharp, Mol. Cell. Biol. 159:601–664 (1982); S. I. Scahill et al, "Expression And Characterization of The Product of a Human Immune Interferon DNA Gene In Chinese Hamster Ovary Cells," *Proc. Natl. Acad. Sci. USA* 80:4654–4659 (1983); G. Urlaub and L. A. Chasin, *Proc. Natl. Acad. Sci. USA* 77:4216–4220 (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Useful expression hosts include well-known prokaryotic and eukaryotic cells. Some suitable prokaryotic hosts include, for example, *E. coli,* such as SG-936 , HB 101, W3110, X1776, X2282, DH1, DH5αF', and MRCl, Pseudomnonas, Bacillus, such as *Bacillus subtilis,* and Streptomyces. Suitable eukaryotic cells include yeasts and other fungi, insect, animal cells, such as COS cells and CHO cells, human cells and plant cells in tissue culture.

C. Fusion Proteins

The proteins of the invention may be expressed in the form of a fusion protein with an appropriate fusion partner. The fusion partner preferably facilitates purification and identification. Increased yields may be achieved when the fusion partner is expressed naturally in the host cell. Some useful fusion partners include beta-galactosidase (Gray, et al., *Proc. Natl. Acad. Sci. USA* 79:6598 (1982)); trpE (Itakura et al., Science 198:1056 (1977)); protein A (Uhlen et al., Gene 23:369 (1983)); glutathione S-transferase (Smith, D. B., Methods Mol. Cell Biol. 4:220–229 (1993); Smith, D. B. and Johnson, K. S., Gene 67:31–40 (1988); Johnson, Nature 338:585 (1989)); Van Etten et al., Cell 58:669 (1989)); and maltose-binding protein (Guan et al., Gene 67:21–30 (1987); Maina et al., Gene 74:36–373 (1988), in Ausubel, F. M. et al. (Eds.) Current Protocols in Molecular Biology, John Wiley & Sons, Inc., New York (1999)).

Such fusion proteins may be purified by affinity chromatography using reagents that bind to the fusion partner. The reagent may be a specific ligand of the fusion partner or an antibody, preferably a monoclonal antibody. For example, fusion proteins containing beta-galactosidase may be purified by affinity chromatography using an anti-beta-agalactosidase antibody column (Ullman, Gene. 29:27–31 (1984)). Similarly, fusion proteins containing maltose binding protein may be purified by affinity chromatography using a column containing cross-linked amylose; see Guan, European Patent Application 286,239.

The protein may occur at the amino-terminal or the carboxy-terminal side of the cleavage site. Optionally, the DNA that encodes the fusion protein is engineered so that the fusion protein contains a cleavable site between the protein and the fusion partner. Both chemical and enzymatic cleavable sites are known in the art. Suitable examples of sites that are cleavable enzymatically include sites that are specifically recognized and cleaved by collagenase (Keil et al., FEBS Letters 56:292–296 (1975)); enterokinase Prickett, K. S. et al., Biotechniques 7:580–589 (1989); LaVallie et al., J. Biol. Chem. 268:23311–23317 (1993)); factor Xa (Nagai et al., Methods Enzymol. 153:461–481 (1987)); and thrombin (Eaton et al., Biochemistry 25:505 (1986) and Chang, J. Y. Eur. J. Biochem. 151:217–224 (1985)). Collagenase cleaves between proline and X in the sequence Pro-X-Gly-Pro wherein X is a neutral amino acid. Enterkinase cleaves after lysine in the sequence Asp-Asp-Asp-Asp-Lys. Factor Xa cleaves after arginine in the sequence Ile-Glu or Asp-Gly-Arg. Thrombin cleaves between arginine and glycine in the sequence Arg-Gly-Ser-Pro.

Specific chemical cleavage agents are also known. For examples, cyanogen bromide cleaves at methionine residues in proteins (Gross, E., Methods Enzymol. 11:238–255 (1967), hydroxylamine cleaves at Asn-Gly bonds (Bormstein, G. and Balian, G., J. Biol. Chem. 245:4854–4856 (1970), and by hydrolysis at low pH (Asp-Pro bonds are labile at low pH; Landon, M., Methods Enzymol. 47(E):145–149 (1977).

D. General Methods for Purification of Proteins

The recombinant protein is purified by methods known in the art. Such methods include affinity chromatography using specific antibodies. Alternatively, the recombinant protein may be purified using a combination of ion-exchange, size-exclusion, and hydrophobic interaction chromatography using methods known in the art. These and other suitable methods are described by Marston, "The Purification of Eukaryotic Proteins Expressed in *E. coli*" in *DNA Cloning*, D. M. Glover, Ed., Volume III, IRL Press Ltd., England, 1987; Guide to Protein Purification, Deutscher, M. P. (Ed.), Methods Enzymol. 182, Academic Press, Inc., New York (1990); Scopes, R. K. and Cantor, C. R. (Eds), Protein Purification (3d), Springer-Verlag, New York (1994); and by Britton, V. J. and Sofer et al. in Biotechniques 1(4), 198–203 (1983).

Materials and Specific Methods

Propagation of Lewis Lung Adenocarcinoma Tumors. C57 B1 mice (Charles River Breeding Laboratories) were provided free access to standard laboratory chow and water. To generate tumors, approximately 1.75×106 Lewis lung mouse carcinoma cells (LL/2, American Type Culture Collection, CRL 1642) were injected subcutaneously into 15 gm C57 B1 females, and the tumors allowed to grow for two weeks before passage. Under light pentobarbitol anesthesia (Membumal, 75 mg/kg body weight), a dorsal incision was made and approximately 3 mm3 of viable tumor cortex was implanted subcutaneously. Tumors were passaged at least three times prior to use. Animals were sacrificed by cervical dislocation, and tumors were removed and stored at $-80°$ C. until use. All animal protocols were approved by the Animal Care and Use Committees of Cornell University Medical College.

Cell Culture. LL/2 cells were grown in 25 cm2 plastic tissue culture flasks (Corning) under 5% CO2 in Dulbecco's Modified Eagles Medium (Mediatech) containing 10% fetal calf serum (Hyclone) and 0.01% penicillin/streptomycin (Gibco Laboratories).

Immunoblots. Cell lysates were resolved by SDS-PAGE on 10% acrylamide, 0.27% bis-acrylamide gels (Ref 34) and electrophoretically transferred to nitrocellulose paper in (40 mM Tris, 240 mM glycine, 20% ethanol, 0.2% SDS) transfer buffer (Ref. 35). Transferred protein was incubated either with a.) 0.1 to 5.0 µg/ml of affinity-purified Anti-DdSev, a polyclonal antibody raised against Dictyostelium severin (Ref. 35), b.) 0.1 to 5.0 µg/ml Anti-MSev, a polyclonal antibody raised against mammalian severin isolated from Lewis lung adenocarcinoma tumors, or c.) 4 µg/ml monoclonal antibody to gelsolin (Sigma). Immunoblots were developed with alkaline phosphatase-conjugated secondary antibody and BCIP-NBT (Promega) following the manufacturer's instructions.

Actin Filament Severing Assays. Rabbit muscle F-actin was used as a substrate for M-severin. Fractions to be assayed for severing activity were added to 0.1 mg/ml F-actin in F-buffer (10 mM triethanolamine, pH 7, 0.2 mM dithiothreitol, 50 mM KCl, 2 mM MgCl2, 1 mM ATP) containing either 0.1 mM CaCl2 (+Ca2+) or 2 mM EGTA (−Ca2+). Mixtures were incubated for 10 min. at 25° C. Aliquots (10 µl) of the reaction mixture were placed on parlodion, carbon-coated grids and stained for 1 min. with 0.2 µm filtered 1% uranyl acetate. Stained grids were blotted on the edge with filter paper, air-dried and viewed in a JEOL 2000 electron microscope at 80 kV accelerating voltage. To quantitate severing efficiency, mixtures resulting from severing assays were centrifuged at 50,000×g for 15 min. to differentially sediment intact actin filaments. Resulting supernatant (actin monomers+fragments) and pelleted (actin filament) fractions were resolved by SDS-PAGE, and the actin and severin content assayed by gel scanning densitometry (Hoeffer, San Francisco, Calif.).

Purification of Mammalian Severin. Isolation of mammalian severin from Lewis lung adenocarcinoma tumors followed the purification method previously established for Dictyostelium severin (Refs. 21,22) with slight modification. Tumor burdens of 15% to 20% of total body weight were excised, rinsed with 5 mM triethanolamine buffer, pH 7.5, and stored at −80° C. until use. All isolation steps were carried out at 4° C. or on ice. For each preparation, approximately 50 gms of tumor tissue was thawed, minced and added to 3 volumes (wt/vol) of cold Lysis Buffer (10 mM triethanolamine, pH 7.5, 60 mM sodium pyrophosphate, 30% (wt/vol) sucrose, and 0.4 mM dithiothreitol). Phenylmethylsulfonylfluoride in ethanol was added to a final concentration of 1 mM and the suspension was immediately sonicated on ice with 3×30 s bursts (Heat Systems W-220F sonicator at 30 MHz power). The cell lysate was centrifuged at 25,000×g for 30 min., and the supernatant fraction was recentrifuged at 150,000×g for 90 min. Total protein concentration was determined for the high speed supernatant fraction Ref (36), and the fraction diluted to 5 mg/ml with cold Lysis Buffer. Triethanolamine (1M, pH 7.5) was added to obtain a final concentration of 50 mM. Solid ammonium sulfate was incrementally added to obtain 60% saturation at 0° C., and the mixture was stirred on ice for 1 hr. After centrifugation at 25,000×g for 30 min., the resulting supernatant fraction was brought to 80% saturation on ice with solid ammonium sulfate. The 80% ammonium sulfate pellet was collected by centrifugation at 25,000×g for 30 min., dissolved in 20 ml DEAE Buffer (2 mM triethanolamine, pH 7.5, 0.2 mM dithiothreitol, 0.005% NaN3) and dialyzed for 24 hr against 3×21. of DEAE Buffer containing 2 mM KCl. The dialyzed fraction was applied to a 1.5×15 cm DEAE cellulose column, (DE 52, Sigma) pre-equilibrated with DEAE Buffer containing 2 mM KCl. Bound protein was eluted at 5 ml/hr in 2.5 ml fractions with a 0–0.6 M KCl linear gradient. Severing activity eluted from 0.05 to 0.15 M KCl. Active fractions were dialyzed overnight against 2×11. HAP Buffer (10 mM KH2PO4, pH 6.7, 0.2 mM dithiothreitol, 0.005% NaN3). The dialyzed fraction was applied to a 1.0×14 cm hydroxylapatite column (Calbiochem) equilibrated with HAP Buffer. Bound protein was eluted at 5 ml/hr in 2.0 ml fractions with a 0–0.6 M KCl linear gradient. Purified M-severin eluted at approximately 0.3 M KCl and was stored on ice until use.

Antibodies. A rabbit polyclonal antibody raised against purified Dictyostelium severin (Ref. 36) was isolated by chromatography through a Zeta Chrom 60 Disk (Cuno, Inc.). Severin-specific IgG (Anti-DdSev) was subsequently affinity-purified using purified Dictyostelium severin crosslinked to a CNBr-activated Sepharose 4B column (Ref. 37). The antibody Anti-MSev was raised in rabbits by subcutaneous injection of purified M-severin from Lewis lung carcinoma tumors. Injection of 2 µg of protein in complete Freund's adjuvant at each of 6 dorsal sites was followed by an equivalent challenge inoculation after two weeks and bleedings at 2 week intervals. Positive sera was stored at −20° C. A monoclonal antibody to human plasma gelsolin showing specificity to an epitope on the 47 kD non-severing chymotryptic peptide (Ref. 38), was purchased from Sigma Chemical Co. (#G 4896).

Cytoimmunofluorescent Localization. LL/2 cells were grown on 15 mm diameter glass coverslips, rinsed with PBS (0.15 M NaCl, 0.015 M Na2HPO4, pH 7.4), fixed by immersion in −20° C. methanol for 10 min., held under PBS for 15 min., and blocked with PBS+1% BSA for 15 min. Coverslips were incubated for 60 min. at 25° C. with 2–3 μg/ml Anti-MSev, washed with PBS (3×10 min.), PBS+1% BSA (15 min.), and incubated with 1.8 μg/ml FITC-conjugated mouse anti-rabbit IgG, F(ab')2 (Jackson ImmunoResearch) for 60 min. at 25° C. F-actin was stained with 0.33 μM rhodamine phalloidin (Molecular Probes) for 60 min. at 25° C. on parallel coverslips. Labeled cells were washed with PBS (3×10 min.) and coverslips mounted on glass slides with gelvatol [15% (w/v) polyvinyl alcohol (Airvol 205, Air Products and Chemicals, Inc.), 65% glycerol (v/v), 35% PBS (v/v)] containing 100 mg/ml 1,4 Diazabicyclo[2.2.2.] Octane (DABCO, Sigma) prior to viewing under a Nikon Microphot microscope.

Confocal Microscopy. LL/2 cells were treated as described for cytoimmunofluorescent staining and 1 μm thick optical sections were examined with a Sarastro 2000 confocal laser scanning microscope (Molecular Dynamics, Sunnyvale, Calif.) using Image Space software.

RNA Isolation and Northern Blot Hybridization. RNA used in Northern analysis was isolated from cultured P19, LL/2 and MDCK cells using the RNeasy Total RNA Kit (Qiagen, Chatsworth, Calif.) according to the manufacturer's instructions. Approximately 50 μg per well of RNA was subjected to electrophoresis through a 1.2% agarose gel containing 2.2 M formaldehyde. RNA was transferred overnight to a positively charged nylon membrane (Boehringer Mannheim, Indianapolis, Ind.) by passive transfer in 20×SSC [1×SSC is 150 mM NaCl, 15 mM sodium citrate (pH 7.0)]. The insert from clone 10 c-1 (0.65 kb) was purified from a 1% agarose gel using the QIAEX II Gel Extraction Kit (Qiagen), labeled with [alpha-32P] dCTP using the Random Primed DNA Labeling Kit (Boehringer Mannheim), and was used as a probe. Hybridization was performed in 50 % formamide, 5×SSPE [1×SSPE is 0.18 M NaCl, 1 mM EDTA, 10 mM NaH2PO4 (pH 7.5)], 0.2% SDS, 5×Denhardt's (39), and 100 μg/ml denatured salmon sperm DNA at 42° C. overnight. The hybridized membrane was rinsed twice at room temperature in 2×SSC/0.1% SDS, and then washed twice at 42° C. in 0.5×SSC/0.1% SDS for 30 min. The Membrane was exposed to a phosphor screen (Molecular Dynamics, Sunnyvale, Calif.) and images of the original radioactive samples were produced with a Phosphorlmager (Molecular Dynamics). The data was analyzed using Molecular Dynamics ImageQuant software version 3.0.

Immunohistochemistry. Paraffin embedded surgical sections of a moderately differentiated adenocarcinoma of the large bowel were sectioned and stained for M-severin with a Vectastain Elite ABC Kit (Vector Laboratories) using biotinylated anti-rabbit IgG as the secondary antibody with peroxidase substrate. Sections were deparaffinized, hydrated through an alcohol series, blocked with rabbit serum, incubated with primary antibodies against either purified *Dictyostelium discoideum* severin or M-severin isolated from Lewis lung carcinoma tumors from C57 mice. Primary antibodies were used at 1:200 for D.d. severin or at 1:50 for LL2 M-severin. Secondary antibody was at 1:200. M-severin stained sections were counterstained with hematoxylin.

Other Methods. Tris-glycinate SDS-PAGE was performed according to Laemmli and Favre (Ref. 34) using 1 mm thick slab gels. Molecular weight standards (Pharmacia) were phosphorylase b (94 kDa), bovine serum albumin (68 kDa), ovalbumin (43 kDa), carbonic anhydrase (30 kDa), soybean trypsin inhibitor (20 kDa) and a-lactalbumin (14 kDa). Protein concentrations were measured by the method of Bradford (40) using bovine plasma gamma globin as a standard. Gels for Western blots were stained with Coomassie Brilliant Blue G250. Free Ca2+ concentration was calculated using a Kd for Ca2+ EGTA of $2 \times 10^{-7}$ M (Ref. 41).

Immunologic Detection of Severin in Lewis Lung Carcinoma Tumors. The requirement for cell migration in epithelial malignancy prompted a survey for severin in LL/2 cell Lewis lung carcinoma tumors. An antibody raised against Dictyostelium severin (Anti-DdSev) (Ref. 35) specifically detected a 40 kDa protein in both Dictyostelium and tumor cell lysates. Antibody avidity was 1000-fold greater for Dictyostelium severin, with positive Western blots obtained with 1 ng/ml Anti-DdSev compared to 1 μg/ml for the 40 kDa protein in tumor lysates.

Isolation of Severin from Tumors. To establish functional identity, the 40 kDa tumor protein was purified from LLC tumors by methods previously established to isolate severin from Dictyostelium amoebae (Refs. 21,22). Isolation utilized ammonium sulfate fractionation of a clarified tumor lysate followed by DEAE and HAP chromatography. Purification was followed by both Ca2+-activated actin filament severing activity and immunoblots with Anti-DdSev. Final HAP chromatography produced a purified 40 kDa protein with Ca2+-activated severing activity and cross-reactivity to Anti-DdSev. The average yield of severin was 0.36 mg per 50 gms of tumor, representing 0.03% of total lysate protein. Like Dictyostelium severin, the tumor protein was completely soluble in 80% ammonium sulfate and eluted from HAP in 0.3 M KCl to give a pure product. However, the isolated mammalian severin was not biochemically identical to Dictyostelium severin, since M-severin showed a moderate affinity to DEAE at pH 7.5 compared to no affinity for Dictyostelium severin.

Functional Activity of M-severin. The actin filament fragmenting activity of purified tumor-derived severin was assayed by electron microscopy and differential sedimentation of various stoichiometric mixtures of severin and F-actin in the presence or absence of 50 μM Ca2+. Actin filaments remained intact in severin:actin mixtures in the absence of Ca2+ (presence of 2 mM EGTA), but were rapidly fragmented upon addition of Ca2+. Like Dictyostelium severin (Ref. 22), increased ratios of M-severin to F-actin produced shorter fragments. At 1:100 M-severin:actin, fragment length averaged 30 nm, compared to an average length of 10.5 nm for 1:20 severin:actin. Fragment lengths corresponded to an average of 130 G-actin subunits in 1:100 fragments and 28 subunits in 1:20 fragments, indicating a stoichiometric rather than catalytic fragmenting activity by M-severin. Isolated M-severin did not induce coaligiment, bundling or cross-linking of actin filaments, suggesting an exclusive fragmentation and capping activity.

To quantitate severing function, increasing ratios of severin:actin were sedimented at 50,000×g for 15 min. to separate short fragments from long fragments and filaments. Gel electrophoresis of separated filaments and fragments confirmed that M-severin action mimicked that of Dictyostelium severin, with enhanced fragmentation at higher ratios of severin: F-actin. Based on close similarities in size, immunologic cross-reactivity, purification properties and functional activity, M-severin has been identified as the mammalian homolog of Dictyostelium severin.

Selective Expression of M-Severin in Transformed Tissues. M-severin expression was compared in normal and transformed tissues. M-severin protein was not detected in normal skeletal muscle, liver, or lung taken from tumorbearing animals. Since Lewis lung carcinoma tumors derive from pulmonary epithelium, it was of considerable interest to directly assay LLC tumors and normal lung tissue from the same animal for M-severin expression. Tumors showed extensive expression of M-severin in both the proliferating tumor cortex and necrotic core, while normal lung showed no cross-reactivity with Anti-DdSev, suggesting M-severin induction in neoplastic C57 B1 mouse lung epithelium.

Comparative Expression of M-Severin and Gelsolin in Normal and Transformed Epithelial Cells. Since severin and gelsolin both function as actin filament severing proteins, severin and gelsolin expression patterns were compared in normal lung and LLC tumors. To maximize sensitivity and specificity, a polyclonal antibody (Anti-MSev) was raised against purified M-severin isolated from mouse tumors. High levels of gelsolin were detected in normal lung lysates together with minute amounts of M-severin. Because highly motile fibroblasts, macrophages and neutrophils in pulmonary connective tissue contain M-severin (unpublished observations), pneumocytes comprising the predominant lung epithelial cell type are not likely to contain the protein. M-severin is immunologically distinct from the N-terminal severin-like domain of gelsolin as evidenced by the lack of cross-reactivity between the Anti-MSev antibody and gelsolin in lung. The appearance of M-severin in transformed tissues cannot be ascribed to a proteolytic breakdown product of gelsolin. In transformed LL/2 tumor cells, expression of M-severin corresponded to a complete loss of gelsolin. We therefore posit that M-severin replaces gelsolin during epithelial cell transformation.

Anti M-sev was also used to clone a partial length M-severin cDNA from a P19 carcinoembryonic cell library (Stratagene). The clone, 10c-1 contained an 135 amino acid sequence (SEQ ID NO.:1) with 48% homology to Dictyostelium severin. See FIG. 1. The clone allowed an analysis of the expression of M-severin mRNA in 3 epithelial cell lines (MDCK, LL/2 and P19 cells) having different metastatic potentials. Quantitation of blots by phosphoimaging (Molecular Dynamics) showed that highly metastatic P19 carcinoembryonic cells expressed approximately 10× as much M-severin mRNA as weakly metastatic LL/2 cells, which in turn showed 7× more mRNA than cultured MDCK cells (FIG. 2). M-severin expression in MDCK cell lines was approximately 70-fold less than in P19 cells. The low, but detectable, basal level of M-severin mRNA expression in MDCK cell cultures may reflect the partially transformed immortalized state of these cells. M-severin is consequently not exclusive to LL/2 cells, but is expressed in 3 different transformed epithelial cell types. Furthermore, M-severin messenger RNA expression showed a strong positive correlation with the metastatic potential of the cell line analysed.

Figure 3:
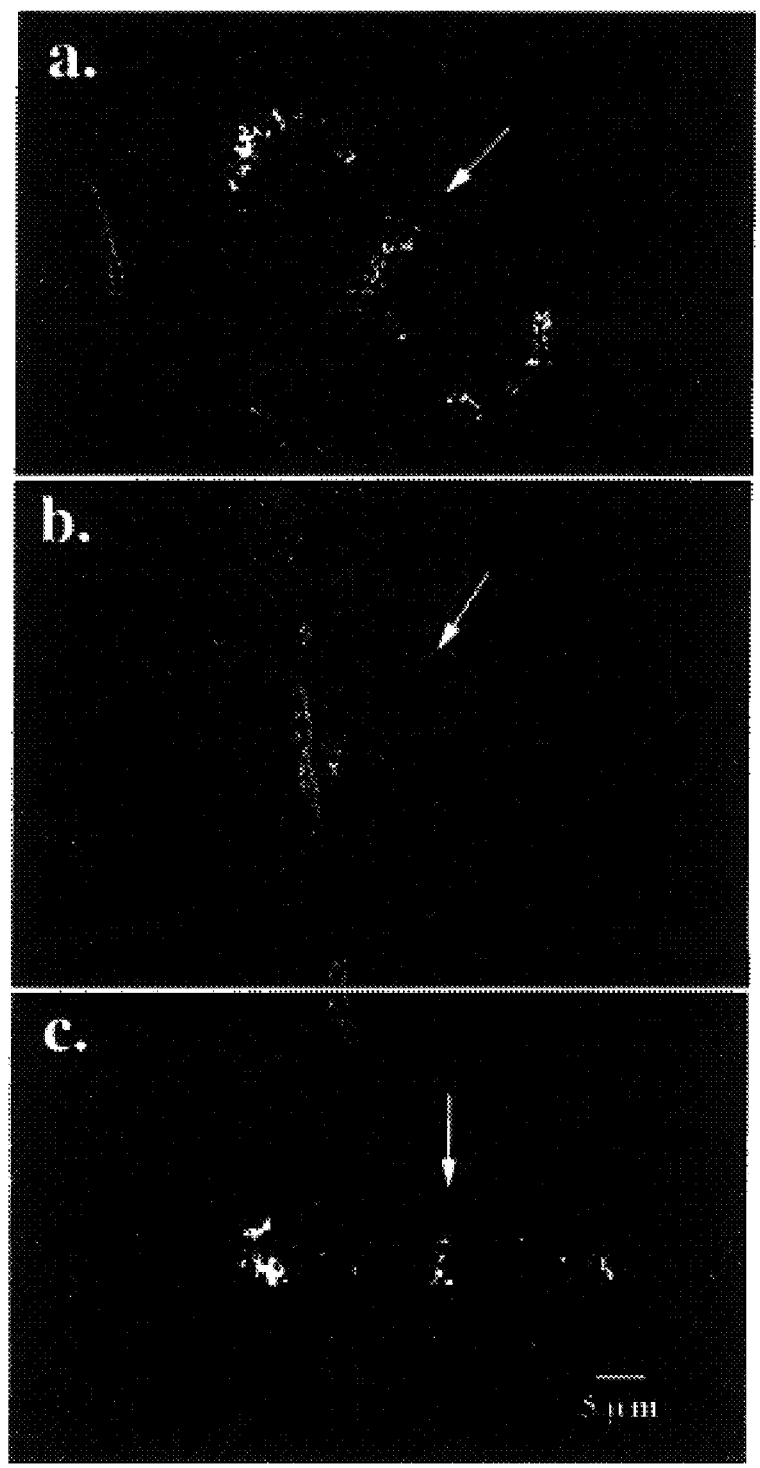
FIG. 3. Localization of M-severin in LL/2 cells. Cultured LL/2 cells labeled for M-severin (FIGS. 3A and 3C) or F-actin (FIG. 3B) were examined by confocal microscopy.

Localization of M-Severin. The intracellular location of M-severin in the actin cytoskeleton of dividing, migratory LL/2 cells was ascertained by confocal microscopy (FIG. 3). In actively dividing cells, M-severin was concentrated in the cleavage furrow and extending cell cortex distal to the furrow (FIG. 3A), and colocalized with F-actin (FIG. 3B). A vertical section through the dividing cell pair shown in FIG. 3A clearly shows high concentrations of M-severin at the leading cell edges and in the cleavage furrow (FIG. 3C). Mammalian severin and F-actin appear colocalized and concentrated in areas actively undergoing actin cytoskeleton rearrangements, consistent with severin localization in Dictyostelium (Ref. 36).

Figure 4:
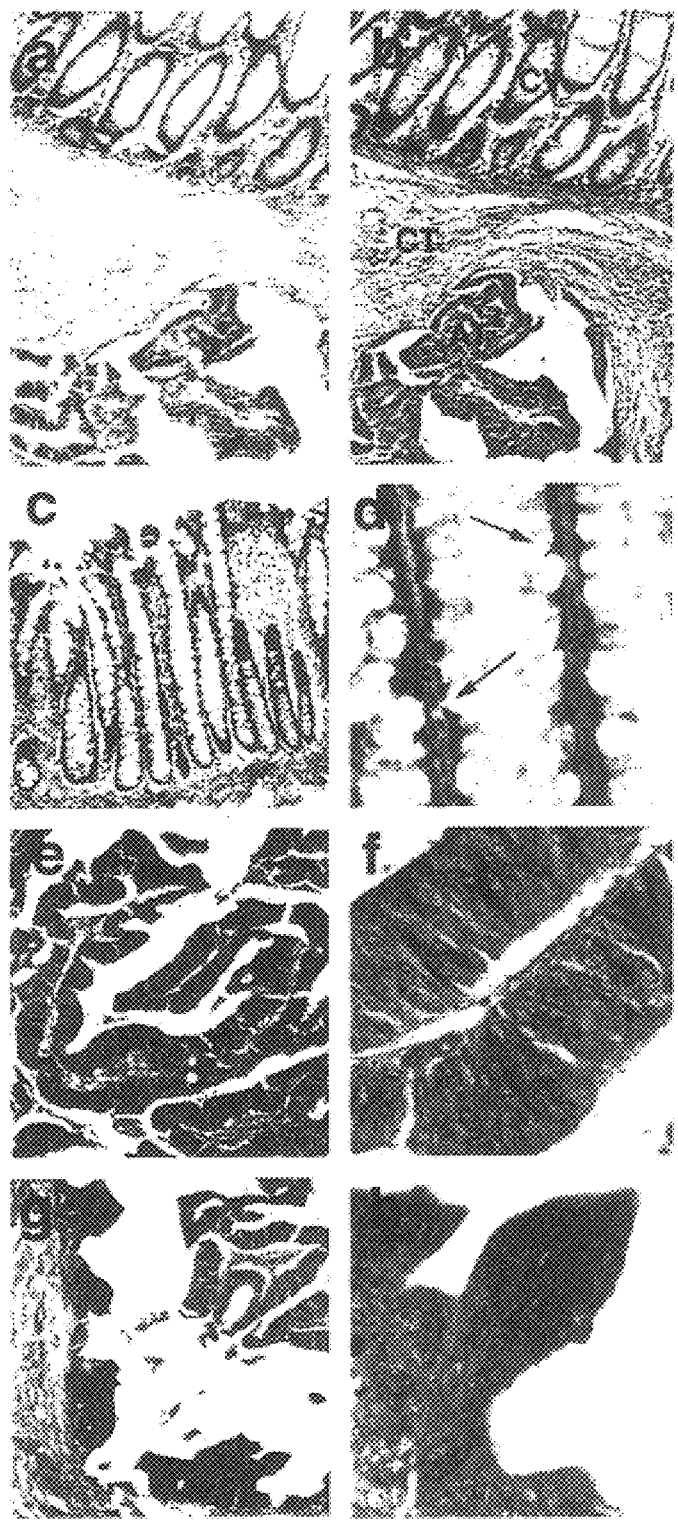
FIG. 4. Expression of M-severin in human colon adenocarcinomas. Resected adenocarcinoma tumors from 2 patients were examined for the presence of M-severin in tranformed epithelium and in motile cells of the colonic connective tissue.

Specific Expression of M-Severin in Invasive Colon Adenocarcinoma. That M-severin is expressed in epithelial carcinomas, but not normal epithelium, was demonstrated by immunohistochemical staining of adenocarcinomas of the colon (FIGS. 4A, 4B) from 2 different patients. Sections through a surgically resected colon showed that M-severin was not expressed in normal colon epithelium (FIG. 4C, 4D, arrows) from the cancer patient. Epithelial cells of normal colonic villi showed no severin staining (FIG. 4D, arrows), while motile connective fibroblasts of the lamina propria underlaying the epithelium contained M-severin (FIG. 4D, *). In moderately differentiated adenocarcinoma from the same patient, M-severin was abundantly expressed in transformed epithelial cells comprising the tumor (FIG. 4E, F). Furthermore, advanced stages of undifferentiated adenocarcinoma existing adjacent to moderately differentiated adenocarcinoma heavily expressed M-severin (FIG. 4G, arrow, FIG. 4H) suggesting that the extent of M-severin expression marks advancing stages of epithelial transformation. The striking up-regulation of M-severin in invasive carcinoma follows the paradigm of M-severin expression in motile, dividing cells documented in cell culture, and portends a significant potential use of M-severin as a marker for stage-specific diagnosis of carcinoma tumors. Similar detection of epithelial transformation by a M-severin marker has been observed in colon polyps and mammary ductal carcinoma.

Discussion

The detection of a mammalian severin significantly broadens the occurrence of a protein previously presumed to be expressed only in Dictyostelium amoebae and Physarum slime molds (fragmin). Severin has traditionally been considered ancestral to gelsolin, the 80 kD F-actin fragmenting protein in mammalian cells, because of extensive sequence homology (Refs. 15,13,42), and because gelsolin is not expressed in Dictyostelium amoebae (Refs. 38,43). Expression of a mammalian severin presents the case for evolutionary conservation of a distinct severin gene. The gene product shows strong immunologic and functional identity to Dictyostelium severin, and shares a common cellular location in the actin-rich cortex. However, M-severin does not derive from a proteolytic breakdown product of gelsolin, since antibodies specific for M-severin do not recognize gelsolin. Two other actin associated proteins, gCap 39 (Refs. 44,45,46) and Mbh1 (Ref. 47), with Mr's approximating M-severin have been described in mammalian cells, but do not function as F-actin fragmenting proteins. Based on sequence similarity, MCP, gCap39, Mbh1, gelsolin, villin and actin binding protein (ABP) all belong to a family of mammalian actin filament regulatory proteins evolved from a structural motif composed of 120–130 amino acids found in Dictyostelium severin (Refs. 13,15,16,48). We propose that M-severin itself now be added to the family of actin-regulatory proteins expressed in mammalian cells.

Although severin has been implicated in Dictyostelium cell motility by its Ca2+-activated F-actin severing function (Refs. 21,22) and restricted localization to extending pseudopods (Ref. 36), the definitive function of severin in migrating amoebae has not been determined. This is largely due to the inability to produce a non-motile phenotype in Dictyostelium mutants lacking severin. The precise function of actin fragmentation in highly motile transformed mammalian cells is also problematic because gelsolin, the only fragmentation protein found to date in epithelial cells, is almost completely downregulated during transformation (Refs. 31,32). In fact, a significant number of actin cytoskeleton proteins germane to cell migration and cytokinesis are extensively downregulated in proliferating and migrating cancer cells, Tropomyosins (Refs. 49–52), profilin (Ref 53), ABP (Ref. 53), caldesmon (Ref. 54) and gelsolin are all substantially diminished or deleted. Especially puzzling has been the disappearance of gelsolin from highly motile transformed human fibroblasts, epithelial cells (Ref. 31) and human breast carcinoma tissue (Ref. 32), because enhanced rates of cell migration are known to occur in fibroblasts overexpressing gelsolin (Ref. 28).

Our demonstration of M-severin inductilon in transformed epithelial cells not only resolves the apparent paradox of down-regulation of actin filament regulatory proteins in neoplastic cell types, but also provides a natural model system for testing phenotypes resulting from M-severin expression in epithelial cells. Induction of expression of M-severin in normal epithelium and knockout of M-severin in transformed epithelial cells may provide key insights into the functional role of actin filament severing in mammalian cells that has not been possible to define.

Expression of M-severin in LL/2 cells is generalized to other motile mammalian cells and to human carcinoma tumors. In moderately differentiated colon adenocarcinomas, cytoimmunostaining for M-severin is apparent in connective tissue fibroblasts as well as invasive epithelial cells. Western blot and cytoimmunostaining for M-severin has also been obtained from mouse carcinoma tumors, 3T3 fibroblasts, activated lymphocytes and macrophages (data not shown), leading to our hypothesis that actin cytoskeleton proteins dedicated to motility and cytokinesis are specifically expressed during epithelial cell transformation and leucocyte activation. Messenger RNA expression patterns of M-severin during transformation further demonstrate a correlation between M-severin expression and progressive metastatic potential of epithelial cell lines. Cloning of the full-length cDNA will be required for unequivocal definition of the function of M-severin in mammalian cells and its role in the acquisition of motility during epithelial celltransformation.

This work provides the initial observation of the replacement of an actin regulatory protein in sessile epithelial cells with one of similar function from a highly motile cell type. We posit that alternate cytoskeletal gene expression may constitute a general biological mechanism for enhancing the migratory and proliferative potential of transformed epithelium and leucocytes. This hypothesis is lent credence by our observation that M-severin becomes selectively expressed in transformed, invasive epithelium in adenocarcinomas of the colon.

Those of skill in the art will recognize the utility and the scope of the invention herein described and its applications in qualitative assays, quantitative assays and screening assays (including high throughput, mass screening and small scale or individual assays). One of skill in the art will also recognize the uses of the present invention in the identification and development of novel drug candidates for the acceleration of wound healing and the management or treatment of disorders of the regulation cytoskeletal structures within the cell including those which lead to neoplastic disease.

References

1. Raz, A., and A. Ben-Ze'ev. 1987. Cell-contact and architecture of malignant cells and their relationship to metastasis. *Cancer and Metastasis Reviews.* 6: 3–21.
2. Liotta, L. A., P. S. Steeg, and W. G. Stetler-Stevenson. 1991. Cancer metastasis and angiogenesis: an imbalance of positive and negative regulation. *Cell.* 64: 327–336.
3. Van Roy, F. V., and M. Mareel. 1992. Tumor invasion: effects of cell adhesion and motility. *Trends Cell Biol.* 2: 163–169.
4. Weiss, L. 1985. Principles of Metastasis. Academic Press, Inc., Orlando, Fla. p. 26.
5. Stossel, T P., C. Chaponnier, P. M. Ezzell, J. H. Hartwig, P. A. Janmey, D. J. Kwiatkowski, S. E. Lind, D. B. Smith, F. S. Southwick, H. L. Yin, and K. S. Zaner. 1985. Nonmuscle actin-binding proteins. *Annu. Rev. Cell Biol.* 1: 353–402.
6. Pollard, T., and J. A. Cooper. 1986. Actin and actin-binding proteins. A critical evaluation of mechanisms and functions. *Annu. Rev. Biochem.* 55: 987–1035.
7. Korn, E. D., and J. A. Hammer. 1988. Myosins of non-muscle cells. *Annu. Rev. Biophys. Biophys. Chem.* 17: 23–45.
8. Bray, D., and J. G. White. 1988. Cortical flow in animal cells. *Science.* 239: 883–888.
9. Stossel, T. P. 1989. From signal to pseudopod. *J. Biol. Chem.* 264: 18261–18264.
10. Condeelis, J., A. Bresnick, M. Demma, S. Dharmawardhane, R. Eddy, A. L. Hall, R. Sauterer, and V. Warren. 1990. Mechanisms of amoeboid chemotaxis: an evaluation of the cortical expansion model. *Dev.-Genet.*, 11: 333–340.
11. Lauffenburger, D. A., and A. F. Horwitz. 1996. Cell migration: a physically integrated molecular process. *Cell.* 84: 359–369.
12. Ampe, C., and J. Vandekerckhove, 1987. The F-actin capping proteins of *Physarum polycephalum:* cap42(a) is very similar, if not identical, to fragmin and is structurally and functionally very homologous to gelsolin:cap42(b) is Physarum actin. *EMBO(Eur. Mol. Biol. Organ.) J.* 6: 4149–4157.
13. Andre, E., F. Lottspeich, M. Schleicher, and A. Noegel. 1988. Severin, gelsolin, and villin share a homologous sequence in regions presumed to contain F-actin severing domains. *J. Biol. Chem.* 263: 722–727.
14. Kwiatkowski, D. J., T. P. Stossel, S. H. Orkin, J. E. Mole, H. R. Colten, and H. L. Yin. 1986. Plasma and cytoplasmic gelsolins are encoded by a single gene and contain a duplicated actin-binding domain. *Nature (Lond).* 323: 455–458.
15. Way, M., and A. G. Weeds. 1988. Nucleotide sequence of pig plasma gelsolin. Comparison of protein sequence with human gelsolin and other actin-severing proteins shows strong homologies and evidence for large internal repeats. *J. Mol. Biol.* 203: 1127–1133.
16. Bazari, W. L., P. Matsudaira, M. Wallek, T. Smeal, R. Jakes, and Y. Ahmed. 1988. Villin sequence and peptide map identify six homologous domains. *Proc. Natl. Acad. Sci. USA.* 85: 4986–4990.
17. Bamburg, J. R., H. E. Harris, and A. G. Weeds. 1980. Partial purification and characterization of a depolymerizing factor from brain. *FEBS (Fed. Eur. Biochem. Soc.) Lett.* 121: 178–182.
18. Mabuchi, I. 1983. An actin-depolymerizing protein (depactin) from starfish oocytes: properties and interaction with actin. *J. Cell Biol.* 97: 1612–1621.
19. Nishida, E., E. Muneyuki, S. Maekawa, Y. Ohta, and H. Sakai. 1985. An actin depolymerizing protein (destrin) from porcine kidney. Its action on F-actin containing and lacking tropomyosin. *Biochemistry.* 24: 6624–6630.
20. Cooper, J. A., J. D. Blum, R. C. Williams, Jr., and T. D. Pollard. 1986. Purification and characterization of actophorin, a new 15,000-dalton actin binding protein from *Acanthamoeba castellanii. J. Biol. Chem.* 261: 477–485.
21. Brown, S. S., K. Yamamoto, and J. A. Spudich. 1982. A 40,000-dalton protein from *Dictyostelium discoideum* affects assembly properties of actin in a Ca2+-dependent manner. *J. Cell Biol.* 93: 205–210.

22. Yamamoto, K., J. D. Pardee, J. Reidler, L. Stryer, and J. A. Spudich. 1982. Mechanism of interaction of Dictyostelium severin with actin filaments. *J Cell Biol.* 95: 711–719.

23. Hasegawa, T., S. Takahashi, H. Hayashi, and S. Hatano. 1980. Fragmin: a calcium ion sensitive regulatory factor on the formation of actin filaments. *Biochemistry.* 19: 2677–2683.

24. Andre, E. A., M. Brink, G. Gerisch, G. Isenberg, A. Noegel, M. Schleicher, J. E. Segall, and E. Wallraff. 1989. A Dictyostelium mutant deficient in severin, an F-actin fragmenting protein, shows normal motility and chemotaxis. *J. Cell Biol.* 108: 985–995.

25. Weeds, A., and S. Maciver. 1993. F-actin capping proteins. *Curr. Opinion Cell Biol.* 5: 63–69.

26. Way, M., B. Pope, and A. G. Weeds. 1992. Evidence for functional homology in the F-actin binding domains of gelsolin and a-actinin: Implications for the requirements of severing and capping. *J. Cell Biol.* 119: 835–842.

27. McLaughlin, P. J., J. T. Gooch, H. G. Mannherz, and A. G. Weeds. 1993. Structure of gelsolin segment 1-actin complex and the mechanism of filament severing. *Nature.* 364: 685–692.

28. Cunningham, C. C., T. P. Stossel, and D. J. Kwiatkowski. 1991. Enhanced motility in NIH 3T3 fibroblasts that overexpress gelsolin. *Science.* 251: 1233–1236.

29. Cox, D., J. Condeelis, D. Wessels, D. Soll, H. Kern, and D. A. Knecht. 1992. Targeted disruption of the ABP-120 gene leads to cells with altered motility. *J. Cell Biol.* 116: 943–55.

30. Cunningham, C. C., J. B. Gorlin, D. J. Kwiatkowski, J. H. Harwig, P. A. Janmey, H. R. Byers, and T. P. Stossel. 1992. Actin-binding protein requirement for cortical stability and efficient locomotion. *Science.* 255: 325–327.

31. Vandekerckhove, J., G. Bauw, K. Vancompernolle, B. Honore, and J. Celis. 1990. Comparative two-dimensional gel analysis and microsequencing identifies gelsolin as one of the most prominent down-regulated markers of transformed human fibroblast and epithelial cells. *J. Cell Biol.* 111: 95–102.

32. Chaponnier, C., and G. Gabbiani. 1989. Gelsolin modulation in epithelial and stromal cells of mammary carcinoma. *Amer. J. Pathol.* 134: 597–603.

33. Jones, J. G., J. Segall, and J. Condeelis. 1991. Molecular analysis of amoeboid chemotaxis: parallel observations in amoeboid phagocytes and metastatic tumor cells. *Experientia-Suppl.* 59: 1–16.

34. Laemmli, U. K., and M. Favre. 1973. Maturation of the head of bacteriophage T4. *J. Mol. Biol.* 80: 575–599.

35. Towbin, H., T. Straehelin, and J. Gordon. 1979. Electrophoretic transfer of proteins from polyacrylamide gels to nitrocellulose sheets: procedure and some applications. *Proc. Natl. Acad. Sci. USA.* 76: 4350–4354.

36. Brock, A. M., and J. D. Pardee. 1988. Cytoimmunofluorescent localization of severin in Dictyostelium amoebae. *Dev. Biol.* 128: 30–39.

37. Johns, J. A., A. M. Brock, and J. D. Pardee. 1988. Colocalization of F-actin and 34-kilodalton actin bundling protein in Dictyostelium amoebae and cultured fibroblasts. *Cell Motility and the Cytoskeleton.* 9: 205–218.

38. Chaponnier, C., P. A. Janmey, and H. L. Yin. 1986. The actin filament-severing domain of plasma gelsolin. *J. Cell Biol.* 103: 1473–1481.

39. Sambrook, J., Fritsch, E. F., and Maniatis, T. 1989. Molecular Cloning: A Laboratory Manual, Second Edition. Cold Spring Harbor Laboratory Press, Cold Spring Harbor, N.Y. pp. 18.17–18.18.

40. Bradford, M. M. 1976. A rapid and sensitive method for the quantitation of microgram quantities of protein utilizing the principle of protein-dye binding. *Anal. Biochem.* 72: 248–254.

41. Tonomura, Y., S. Watanabe, and M. Morales. 1969. Conformational changes in the molecular control of muscle contraction. *Biochemistry.* 8: 2171–2176.

42. Vandekerckhove, J. 1989. Structural principles of actin-binding proteins. *Curr. Opinion Cell Biol.* 1: 15–22.

43. Folger, P. A. 1996. Identification and characterization of M-severin, an actin filament severing protein in murine carcinoma tumors. [Ph.D. Thesis]. New York, (N.Y.): Cornell University. Available from: UMI Dissertation Services, Ann Arbor, Mich.

44. Yu, F., P. A. Johnston, T. C. Sudhof, and H. L. Yin. 1990. gCap39, A calcium ion- and polyphosphoinositide-regulated actin capping protein. *Science.* 2: 1413–1415.

45. Southwick, F. S., and M. J. DiNubile. 1986. Rabbit alveolar macrophages contain a Ca2+-sensitive, 41,000-dalton protein which reversibly blocks the "barbed" ends of actin filaments but does not sever them. *J. Biol. Chem.* 261: 14191–14195.

46. Young, C. L., F. S. Southwick, and A. Weber. 1990. Kinetics of the interaction of a 41-kilodalton macrophage capping protein with actin: Promotion of nucleation during prolongation of the lag period. *Biochenmistry.* 29: 2232–2240.

47. Prendergast, G. C., and E. B. Ziff. 1991. Mbh1: a novel gelsolin/severin-related protein which binds actin in vitro and exhibits nuclear localization in vivo. *EMBO J.* 10: 757–766.

48. Arpin, M., E. Pringault, J. Finidori, A. Garcia, J. M. Jeltsch, J. Vandekerckhove, and D. Louvard. 1988. Sequence of human villin: a large duplicated domain homologous with other actin-severing proteins and a unique small carboxy-terminal domain related to villin specificity. *J. Cell Biol.* 107: 1759–1766.

49. Hendricks, M., and H. Weintraub. 1981. Tropomyosin is decreased in transformed cells. *Proc. Natl. Acad. Sci. USA.* 78: 5633–5637.

50. Matsumura, F., J. J. C Lin, S. Yamashiro-Matsumura, G. P. Thomas, and W. C. Topp. 1983. Differential expression of tropomyosin forms in the microfilaments isolated from normal and transformed rat cultured cells. *J. Biol. Chem.* 258: 13954–13964.

51. Leavitt, J., G. Latter, L. Lutomski, D. Goldstein, and S. Burbeck. 1986. Tropomyosin isoform switching in tumorigenic human fibroblasts. *Mol. Cell. Biol.* 6: 2721–2726.

52. Celis, G., G. P. Ratz, P. Madsen, B. Gesser, J. B. Lauridsen, K. P. Brogaard Hansen, S. Kwee, H. Holm Rasmussen, H. V. Nielsen, D. Cruger, B. Basse, H. Leffers, B. Honore, O. Moller, and A. Celis. 1989. Computerized, comprehensive databases of cellular and secreted proteins from normal human embryonic lung MRC-5 fibroblasts: identification of transformation and/or proliferation sensitive proteins. *Electrophoresis.* 10: 76–115.

53. Kwiatkowski, D. J. 1988. Predominant induction of gelsolin and actin-binding protein during myeloid induction. *J. Biol. Chem.* 263: 13857–13862.

54. Koji-Owada, M., A. Hakura, K. Iida, I. Yahara, K. Sobue, and S. Kakiuchi. 1984. Occurrence of caldesmon (a calmodulin-binding protein) in cultured cells: Comparison of normal and transformed cells. *Proc. Natl. Acad. Sci. USA.* 81: 3133–3137.

What is claimed is:

1. An isolated human actin-binding regulatory protein which is expressed in motile, proliferating, and invasive cells, and in cells at the site of a wound.

2. The isolated human actin-binding regulatory protein of claim 1 which protein is human M-severin.

3. The isolated human actin-binding regulatory protein of claim 1 which protein is human M-30.

4. The isolated protein of claim 1 comprising an amino acid sequence which is at least 95% homologous to SEQ ID NO:1 of M-severin protein.

5. The isolated protein of claim 1 capable of severing F-actin filaments.

6. The isolated protein of claim 1 isolated from a eukaryotic cell.

7. The isolated protein of claim 1 which is expressed from a 1.9 Kb mRNA.

8. The isolated protein of claim 1 which is expressed by a motile cell or a neoplastically transformed cell.

9. The isolated protein of claim 1 which is expressed by a proliferating cell or a tumor cell.

10. The isolated protein of claim 1 which is a native protein.

11. The isolated protein of claim 1 which is a recombinant protein.

* * * * *

UNITED STATES PATENT AND TRADEMARK OFFICE
CERTIFICATE OF CORRECTION

PATENT NO. : 6,403,766 B1  Page 1 of 2
DATED : July 25, 2002
INVENTOR(S) : J. D. Pardee It is certified that error appears in the above-identified patent and that said Letters Patent is hereby corrected as shown below:

Column 11,
Line 24, now reads "197-193", should read -- 187-193 --
Line 32, now reads "adenoviris, cytomegalovirus (CMV) retrovinis-derived DNA", should read -- adenovirus, cytomegalovirus (CMV) retrovirus-derived DNA --
Line 44, now reads "Kaufynann", should read -- Kaufmann --

Column 12,
Line 5, now reads "Pseudomnonas", should read -- Pseudomonas --
Line 33, now reads "agalactosidase", should read -- galactosidase --
Line 63, now reads"Bormstein", should read -- Bornstein --

Column 13,
Line 56, now reads "MgC112", should read -- MgC12 --

Column 16,
Line 51, now reads "coaligiment", should read -- coalignment --

Column 19,
Line 8, now reads "inductilon", should read -- induction --

Column 21,
Line 48, now reads "Experientiα-Suppl.", should read -- Experientia-Suppl. --

UNITED STATES PATENT AND TRADEMARK OFFICE
CERTIFICATE OF CORRECTION

PATENT NO. : 6,403,766 B1
DATED : July 25, 2002
INVENTOR(S) : J. D. Pardee

It is certified that error appears in the above-identified patent and that said Letters Patent is hereby corrected as shown below:

<u>Column 22,</u>
Line 27, now reads "Biochenmistry", should read -- Biochemistry --
Line 63, now reads "K. lida", should read -- K. Iida --

Signed and Sealed this

Third day of September, 2002

Attest:

JAMES E. ROGAN
Attesting Officer
Director of the United States Patent and Trademark Office